(12) United States Patent
Schwarz et al.

(10) Patent No.: US 9,924,855 B2
(45) Date of Patent: *Mar. 27, 2018

(54) ENDOSCOPIC INSTRUMENT (71) Applicant: Karl Storz SE & Co. KG, Tuttlingen (DE)

(72) Inventors: Peter Schwarz, Tuttlingen-Nendingen (DE); Christina Friedrich, Eutingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 306 days.

This patent is subject to a terminal disclaimer.

(21) Appl. No.: 14/174,999

(22) Filed: Feb. 7, 2014

(65) Prior Publication Data
US 2014/0221751 A1 Aug. 7, 2014

(30) Foreign Application Priority Data
Feb. 7, 2013 (DE) .................. 10 2013 101 202

(51) Int. Cl.
*A61B 1/005* (2006.01)
*A61B 17/00* (2006.01)
(Continued)

(52) U.S. Cl.
CPC ............ *A61B 1/0052* (2013.01); *A61B 1/005* (2013.01); *A61B 1/0016* (2013.01);
(Continued)

(58) Field of Classification Search
CPC ............ A61B 1/00066; A61B 1/00068; A61B 1/00098; A61B 1/00133; A61B 1/0016;
(Continued)

(56) References Cited

U.S. PATENT DOCUMENTS

| 4,499,895 A | 2/1985 | Takayama |
| 4,503,842 A | 3/1985 | Takayama |

(Continued)

FOREIGN PATENT DOCUMENTS

| EP | 1825801 A1 | 8/2007 |
| EP | 2039284 A1 | 3/2009 |

(Continued)

OTHER PUBLICATIONS

"Drehmomentwellenberechnung", Telemetrie-Messtechnik Schnorrenberg, 2009.

(Continued)

*Primary Examiner* — Ryan Henderson
(74) *Attorney, Agent, or Firm* — Whitmyer IP Group LLC (57) ABSTRACT

Endoscopic instrument with a control element, an instrument shaft, an adjustment element, a pull element, an actuator, an intermediate element which is operatively connected to the control element and to the adjustment element such that a force applied to the control element by the user can be transmitted to the adjustment element via the intermediate element in order to move the adjustment element, a detection device for detecting a torsion of the intermediate element, and an abutment device, which defines a free rotatory movement range of the control element relative to the adjustment element.

18 Claims, 5 Drawing Sheets

(51) Int. Cl.
*A61M 25/01* (2006.01)
*A61B 1/00* (2006.01)

(52) U.S. Cl.
CPC ........ *A61B 1/00039* (2013.01); *A61B 1/0051* (2013.01); *A61B 1/00133* (2013.01); *A61B 1/0057* (2013.01); *A61B 2017/00318* (2013.01); *A61B 2017/00323* (2013.01); *A61B 2017/00327* (2013.01); *A61M 25/0136* (2013.01); *A61M 25/0147* (2013.01)

(58) Field of Classification Search
CPC ..... A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 2017/003; A61B 2017/00318; A61B 2017/00323; A61B 2017/00327; A61M 25/0133; A61M 25/0136; A61M 25/0138; A61M 25/0141; A61M 25/0144; A61M 25/0147; A61M 25/0152; A61M 25/0155; A61M 25/0158
USPC ........ 600/117, 118, 145–152, 104, 106, 107; 606/1; 604/95.01–95.05, 523–528
See application file for complete search history.

(56) References Cited

U.S. PATENT DOCUMENTS

| | | |
|---|---|---|
| 4,721,099 A | 1/1988 | Chikama |
| 5,060,632 A | 10/1991 | Hibino et al. |
| 6,932,761 B2 | 8/2005 | Maeda et al. |
| 7,331,924 B2 | 2/2008 | Arai et al. |
| 2004/0034279 A1 | 2/2004 | Arai et al. |
| 2004/0073084 A1 | 4/2004 | Maeda et al. |
| 2007/0255104 A1* | 11/2007 | Maruyama ........... A61B 1/0052 600/148 |
| 2009/0227841 A1 | 9/2009 | Miyako et al. |
| 2010/0125166 A1 | 5/2010 | Henzler |
| 2010/0210908 A1 | 8/2010 | Ashida et al. |
| 2011/0009698 A1 | 1/2011 | Ashida et al. |
| 2011/0065994 A1 | 3/2011 | Kudoh et al. |
| 2011/0088498 A1 | 4/2011 | Ettwein et al. |

FOREIGN PATENT DOCUMENTS

| | | |
|---|---|---|
| EP | 2324755 A1 | 5/2011 |
| JP | 2005028018 A | 2/2005 |
| WO | 2012063880 A1 | 5/2012 |

OTHER PUBLICATIONS

"Messtechnische Übungen II, Messen mit DMS-Aufnehmern", Dipl.-Ing. Johannes Thatn, Technische Universität Berlin, 2006.

"Torsions-Aufnehmer mit DMS-1/2-Brückenanschluss für Temperaturkompensation und R-Abgleich", VISHAY Measurements Group Messtechnik GmbH, 1994.

* cited by examiner

ENDOSCOPIC INSTRUMENT

FIELD OF THE INVENTION

The disclosure relates to an endoscopic instrument with a control section with a control element, also with an instrument shaft with an actuatable portion, wherein the instrument shaft is connected to the control section, an adjustment element, pull element, which is mechanically coupled to the adjustment element and to the portion of the instrument shaft, such that a movement of the adjustment element can cause an actuation of the portion by a transmission of force via the pull element, and also with an actuator, which is coupled to the adjustment element, such that an actuation of the actuator can cause a movement of the adjustment element by force transmission from the actuator to the adjustment element.

BACKGROUND OF THE INVENTION

Endoscopic instruments with a flexible or rigid instrument shaft are used both in industry and also in medicine. For example, flexible endoscopes are used in veterinary medicine for gastro-endoscopic examination of large animals. These endoscopes often have, at a distal end of their instrument shaft, a distal end portion, which finishes in an endpiece. The endpiece represents the distal part of the endoscope that is inserted into the body to be examined. It usually has the distal end of an endoscope lens system and also some of the suction, flushing and instrument channels.

To be able to ensure the greatest possible flexibility as regards a spatial orientation of the endpiece during the examination, the end portion of the instrument shaft is usually configured to be deflectable. By a deflection, or general actuation, of the portion relative to the rest of the instrument shaft, in particular by bending or curving, a part of the instrument shaft, in particular the endpiece, can be given the desired orientation. During this deflection, a user has to proceed carefully in order to ensure that no damage is done to any tissue located around the end portion. It is therefore important that the actuation of the portion can be very precisely controlled.

In flexible and rigid endoscopes according to the prior art, the portion is deflected via a pull element, in particular via Bowden cables. The pull element is connected to an adjustment element, in particular a steering gear. The pull element is often secured on a cord pulley. By actuation of the control element on the control section of the endoscope, the adjustment element is moved. A rotary movement of the adjustment element results in a translational movement of the pull element. The movement of the pull element in turn results in a deflection of the portion.

U.S. Pat. No. 4,499,895 relates to an electrical endoscope, which is controlled via a lever coupled to the adjustment element. When the lever is moved relative to the adjustment element, a flexion of the lever or a change in resistance of a potentiometer is detected and, in this way, the adjustment element is assisted by an actuator. However, the construction shown is very unwieldy and, in the event of a fault, requires a special release mechanism in order to be able to continue operating the endoscope.

U.S. Pat. No. 7,331,924 relates to an electrical endoscope with a deflectable distal portion. The endoscope is controlled in this case using a track ball, of which the movement caused by the thumb or another finger of a user is detected by an electrical circuit. Depending on the rotary movement of the track ball, as chosen by the user, a deflection control system triggers a motor, which causes a movement of the pull element and therefore a deflection of the distal portion.

However, the disadvantage of an electrical endoscope of this kind is that the control feels less intuitive, since the control of an electrical endoscope, e.g. when the latter strikes against tissue, does not provide the kind of feedback, in the form of a counterforce on the control element, that a person receives when using mechanical endoscopes. These problems are also found in electrical endoscopes that are controlled using a joystick. In this connection, reference is made purely by way of example to the document U.S. Pat. No. 6,932,761. Electrical endoscopes also have the disadvantage that, in the event of a defect, it is difficult to withdraw them from the cavity when the distal portion has been deflected.

In mechanical endoscopes, the portion is deflected exclusively by a mechanical force applied by the user to an external handle on the control section of the endoscope. For this purpose, the adjustment element is usually arranged fixedly on a shaft of the handle. When the user actuates the handle, this causes a rotary movement of the adjustment element and therefore in turn the translational movement of the pull element.

However, depending on the endoscope length and on the position of the instrument shaft, purely mechanical endoscopes may require considerable forces for actuating them. Moreover, the mechanical actuation of the portion automatically generates a certain restoring force in the direction of the non-deflected position (zero position) of the endoscope. Furthermore, during the deflection, the portion forms, together with the pull element, a spring/damper system which stores energy when tensioned and releases energy when relaxed. This can result in a start-up idle time or a slow-down in the deflection of the end portion. The effect of this is that, as regards the deflection he would like to confer on the portion in order to be able to view a certain location, the user can obtain this only approximately or iteratively.

SUMMARY OF THE INVENTION

It is an object to improve an endoscopic instrument of the type mentioned at the outset and to develop it in such a way that the user, while obtaining assistance in the control of the endoscope as in the case of an electrical actuation, does not have to do without mechanical feedback via the endoscope. A further object is to ensure that the endoscope can still be operated even in the event of a failure of the electrical control.

There is provided an aforementioned endoscopic instrument with an intermediate element, which is operatively connected to the control element and to the adjustment element such that a force applied to the control element by the user can be transmitted to the adjustment element via the intermediate element in order to move the adjustment element, with a detection device for detecting a torsion of the intermediate element, and with an abutment device, which defines a free rotatory movement range of the control element relative to the adjustment element.

There are a number of different aspects, some in the design of the intermediate element and of the abutment device and in the interaction between control element, intermediate element and adjustment element. In order to illustrate this, some exemplary ways of actuating the endoscopic instrument are explained below.

A first possibility to be considered is that of operation purely by motor. Here, a user actuates the control element in such a way that the control element moves slightly in relation to the adjustment element, in particular moves slightly in rotation. The force applied by the user is transmitted from the control element to the intermediate element. Since the intermediate element is operatively connected to the adjustment element, in particular connected directly thereto, and since the adjustment element does not move at first, this results in a torsion or twisting of the intermediate element, at least of a portion of the intermediate element.

It will be noted at this point that the term "force" is also intended to include a torque, since the latter results in particular from the length of a lever arm multiplied by a force.

The torsion of the intermediate element can be detected by the detection device. In some embodiments not only the presence of a torsion is detected, but also the direction of the torsion, i.e. whether the torsion is clockwise or counterclockwise. In another embodiment, the strength of the torsion is also determined, since this permits a conclusion concerning the force applied by the user.

From knowledge of the torsion, the actuation performed by the user can be inferred. In particular, the actuation direction chosen by the user and/or the force applied by the user can be detected. Since the actuation of the endoscopic instrument as desired by the user is thus detected, the actuator is then triggered in such a way that it moves the adjustment element in the manner desired by the user. For this purpose, the actuator is in operative connection, in some embodiments in direct connection, and in other embodiments in direct mechanical connection, to the adjustment element. The user then controls the endoscopic instrument purely by motor.

In a further possible operating mode, the adjustment element is acted on by a combination of motor actuation and force applied by the user. Once again, a torsion of the intermediate element, at least of a portion of the intermediate element, leads to assistance by motor. Now, however, it is possible for the user to apply such great force that the free rotatory movement range of the control element relative to the adjustment element is exhausted.

This means that the control element mechanically contacts the abutment device. Some of the force applied by the user is then transmitted directly to the adjustment element via the abutment device. This means that the movement of the adjustment element is effected both by the actuator and also by at least some of the force applied by the user. Moreover, it is thus possible to prevent a situation where the force applied by the user causes the intermediate element or a measurement element of the detection device to undergo a plastic deformation that would cause damage. The abutment device thus also constitutes an overload protection.

Finally, an actuation that is brought about exclusively by the force of the user, i.e. purely manually, should be considered. Here, it is assumed that the motor assistance by the actuator is not present. The reason for this may be a failure of the actuator or of its control system or, as is possible in an embodiment, because the user has switched off the motor assistance. In this possible operating mode, a torsion of the intermediate element once again takes place, but no movement of the adjustment element by the actuator. It is therefore necessary that the abutment device provides a force transmission from the control element to the adjustment element, in order for at least most of the force applied by the user to be transmitted to the adjustment element. This is achieved by the fact that the free rotatory movement range of the control element relative to the adjustment element is exhausted. At least most of the force applied by the user is then transmitted directly to the adjustment element via the abutment device.

As will be further explained on the basis of the illustrative embodiments, the abutment device may be formed by two projections on the adjustment element and if a portion of the control element moves between these two projections or bears thereon. In another embodiment, the abutment device is configured as a recess or groove in the adjustment element, and the portion engages with a projection in this recess or this groove. In another embodiment, the abutment device is arranged as a projection on the adjustment element, and the end of the portion is configured in the manner of a fork with two prongs, wherein the projection is arranged between the prongs. Finally, in another embodiment, the abutment device is arranged as a projection on the adjustment element, and the projection engages in a recess or groove of the portion. In another embodiment, the portion is connected directly to the control element, in particular configured in one piece.

It will be noted that the adjustment element can have a plurality of component parts, in particular connection elements and force transmission elements, for example shafts, disks or toothed wheels. In an embodiment, the adjustment element has a cord pulley. In another embodiment, the adjustment element also has a gear, with which a force applied to the adjustment element by the intermediate element is transmitted to the cord pulley.

The intermediate element can be an element separate from control element and adjustment element. In certain embodiments, the intermediate element can also be configured in one piece with the control element or with the adjustment element. In principle, it is also possible for control element, adjustment element and intermediate element to be configured in one piece. In an embodiment, a longitudinal extent of the intermediate element coincides with a rotation axis of the control element and/or a rotation axis of the adjustment element.

In an embodiment, a measurement element of the detection device is arranged on the intermediate element.

This embodiment may permit convenient realization of the detection device. For example, the measurement element can be adhesively bonded onto the intermediate element. In another embodiment conductive plastics are used which, if necessary, are embedded in a flexible insulating material and, in the event of stretching, indicate a change in the electrical resistance. In another embodiment the measurement element is applied as an injection-molded interconnect device (MID) onto the intermediate element. It is also possible for the measurement element, if appropriate including the detection device, to be arranged in the intermediate element, where it is well protected.

In another embodiment, the detection device has a measurement element which is configured in such a way that the electrical resistance of the measurement element changes in the event of a change of shape of the measurement element.

This embodiment may permit simple detection of the torsion by a measuring technique. In addition, the detection device can be made particularly compact. In another embodiment the measurement element used is a conductor or strip conductor which is arranged such that its shape changes, in particular by bending, compressing or stretching, in the event of a torsion of the intermediate element.

In another embodiment, the detection device has a measurement element configured as a strain gauge.

This embodiment may permit cost-effective production of the detection device since, in this connection, there is already extensive theoretical knowledge, practical experience and a large range of available products. Solely by way of example, reference is made to the publication "Messtechnische Übungen II, Messen mit DMS-Aufnehmern", Dipl.-Ing. Johannes Thaten, Technische Universität Berlin, 2006, and to the publication "Drehmomentwellenberechnung", Telemetrie-Messtechnik Schnorrenberg, 2009.

In another embodiment, the detection device has at least two measurement elements which are arranged in such a way that, in the detection device, a compensation is permitted for at least one interference influence chosen from the group consisting of flexion, longitudinal extension and temperature.

This embodiment may allow for the endoscopic instrument to be operated independently or at least substantially independently of environmental influences. As regards temperature compensation, reference is made solely by way of example to the publication "Torsions-Aufnehmer mit DMS-1/2-Brückenanschluss für Temperaturkompensation and R-Abgleich", VISHAY Measurements Group Messtechnik GmbH, 1994.

In another embodiment, the intermediate element has at least a first area and a second area, wherein the first area is made from a different material than the second area.

This embodiment may make it possible to optimize the second area with respect to the desired torsion measurement. For the second area, the materials used in an embodiment are those which can be elastically deformed by slight force and which at the same time remain elastic over a wide range. Substances that are used in some embodiments are from the group of polyarylether ketones, in particular polyether ether ketone (PEEK). Alternatively or in addition, the cross section of the second area can also be varied in relation to the first area, in order to find a good match between actuation force, lever arm, deformation and sufficiently precise measurement signal in the available installation space. In an embodiment, the first area and second area are arranged one after the other along a longitudinal extent of the intermediate element.

In another embodiment, the intermediate element is made from a different material than the control element and/or the adjustment element.

This embodiment may make it possible to optimize the intermediate element with respect to the desired torsion measurement. Independently of this choice of material, the materials for the control element and the adjustment element can be chosen freely, in particular with respect to the requirements placed on the control element and the adjustment element.

In another embodiment, the abutment device is adjustable, in order to vary the movement range.

In this way, it may be possible to individually adjust the extent to which a free rotatory movement of the control element relative to the adjustment element is to be possible before an at least partial transmission of force to the adjustment element via the abutment device takes place. In some embodiments, the free movement range may be chosen to be relatively large, since control purely by motor is then possible within a wide range. In other embodiments, the free movement range is kept small, such that a combination of actuation by a motor and actuation by the force applied by the user takes place at an early stage. The abutment device may be adjusted by using abutment elements in which the position of an abutment surface can be changed, in particular by rotating, screwing or pushing. The statements concerning the choice of the size of the free movement range apply equally to the case where the abutment device is not adjustable.

In another embodiment, the adjustment element has a gear, in particular a gear with a positive transmission ratio.

This embodiment may permit particularly good adjustment of the extent to which the force applied by the user is transmitted to the pull element. The gear may be configured as a combination of external toothed wheel and internal toothed wheel. In another embodiment, the actuator has a gear.

In another embodiment, the first rotation axis of the adjustment element, a second rotation axis of the control element, and a longitudinal axis of the intermediate element coincide.

This embodiment may permit a cost-effective construction and simple transmission of force from the control element to the intermediate element, from the intermediate element to the adjustment element and, if the operation is not purely by motor, from the control element to the adjustment element.

In another embodiment, a first rotation axis of the adjustment element and a third rotation axis of the actuator coincide.

This embodiment may permit a cost-effective construction and simple transmission of force from the actuator to the adjustment element. In particular, a rotation axis of a cord pulley and the third rotation axis of the actuator also coincide.

In another embodiment, the adjustment element has an at least approximately circular support element, on which the abutment device is arranged at least approximately in the circumferential direction of the support element.

This embodiment may permit cost-effective production of the endoscopic instrument and reliable operation. In some embodiments the support element is in direct mechanical contact with the pull element, and in particular if the support element is configured as a cord pulley. In other embodiments, particularly when using a gear, the support element is not in direct mechanical contact with the pull element, in particular that the support element is a component separate from the cord pulley.

In another embodiment, the endoscopic instrument also has a controller configured to detect a measured value of the torsion and to trigger the actuator on the basis of the measured value.

This embodiment may permit a realization of the operation purely by motor or the combined operation. In connection with the detection element, the controller evaluates a measured value or a measured signal which indicates a torsion of the intermediate element. This at least detects that the user wishes to actuate the endoscopic instrument. In an embodiment the direction of the desired actuation is also determined and, in a particular embodiment, also information concerning the force applied by the user. The controller accordingly receives information concerning the fact that the user actuates the endoscopic instrument and, in a particular embodiment, concerning how he actuates it. For this purpose, the controller is configured to trigger the actuator such that the actuation of the endoscopic instrument desired by the user is performed by motor or at least assisted by motor.

It will be appreciated that the aforementioned features and the features still to be explained below can be used not only in the respectively cited combination, but also in other combinations or in isolation, without departing from the scope and spirit of the present disclosure.

BRIEF DESCRIPTION OF THE DRAWINGS

Illustrative embodiments are explained in more detail in the following description and are shown in detail in the drawing, in which.

DETAILED DESCRIPTION OF THE INVENTION

Figure 1:
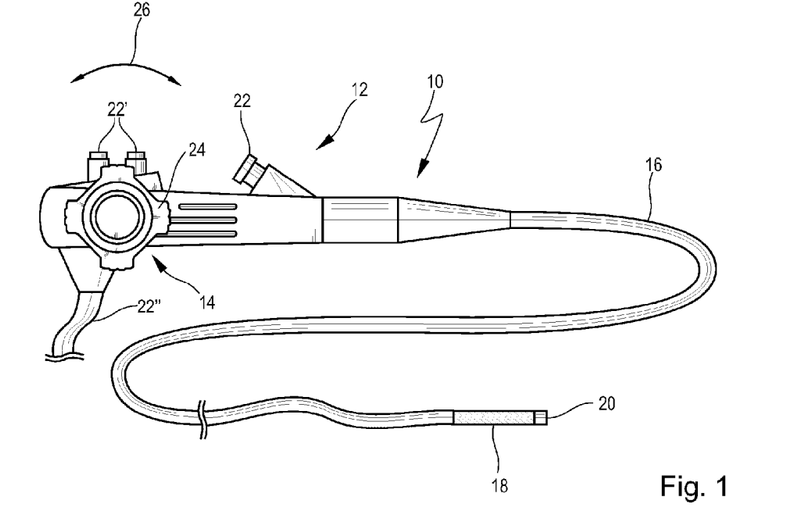
FIG. 1 shows an illustrative embodiment of a flexible endoscope with a deflectable distal portion.

FIG. 1 shows an endoscopic instrument 10 with a control section 12, with a control element 14 and a flexible instrument shaft 16. It will be noted that the explanations given apply in the same way to a rigid instrument shaft (not shown).

The endoscopic instrument 10 is used for exploratory and/or surgical purposes in medical procedures. The instrument shaft 16 contains an endoscope lens system (not shown) in the form of light-guiding fibers, image carriers, various channels, such as a suction channel and flushing channel, and an instrument channel. The instrument shaft 16 is connected at the proximal end to the control section 12 and extends in the distal direction as far as a deflectable portion 18, which in this case is in particular an end portion.

The latter has an endpiece 20 in the form of a closure bushing. The endpiece 20 is the area of the instrument shaft 16 in which the light-guiding fibers, the image carriers and channels end. The instrument shaft 16 is shown only in part in the figures. The control section 12 has a connector 22, buttons 22' and a supply cable 22". The connector 22 leads to an instrument channel. Instruments can be guided through it into the instrument shaft 16 and all the way through the endpiece 20. In this way, for example, operations can be performed in the area in front of the endpiece 20.

The supply cable 22" contains various types of supply lines, for example an electrical supply line, light guides, suction and flushing hoses and/or data links. The imaging of the endoscopic instrument 10 is effected via an image sensor (not shown) in the interior of the control section 12 or in the endpiece 20, wherein the image data are conveyed through the supply cable 22" to the outside, in particular to a camera control unit, or CCU (not shown).

The deflection of the portion 18 is controlled by the control element 14, shown here in an embodiment with a handle 24 that can be turned in the directions of the double arrow 26. The deflectable portion 18 is deflected up/down or left/right when the control element 14 is turned. Here, the deflection corresponds in each case to the direction of rotation of the control element 14, i.e. either counterclockwise or clockwise. In another embodiment, in addition to the control element 14 shown, a further control element (not shown) is used, such that up/down and left/right movements can be combined via a further adjustment element and a further pull element.

Figure 2:
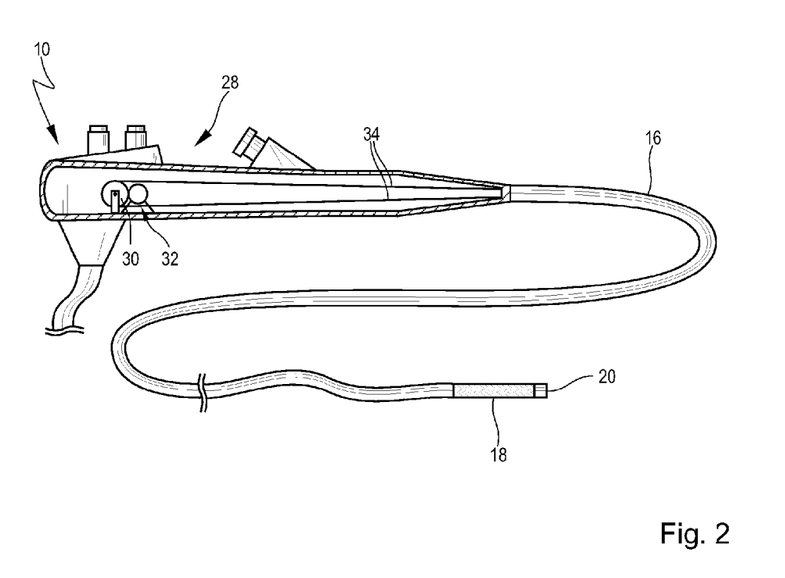
FIG. 2 shows the endoscope from FIG. 1 in a simplified schematic and partially cut-away sectional view.

As is shown in a very simplified manner in FIG. 2, an adjustment element 30 and an actuator 32 are arranged in a proximal end area 28 of the control section 12. The adjustment element 30 is connected to a pull element 34, which is guided through the instrument shaft 16 and extends into the end portion 18. The pull element 34 is guided around a part of the adjustment element 30 and is here configured in one piece.

Figure 3:
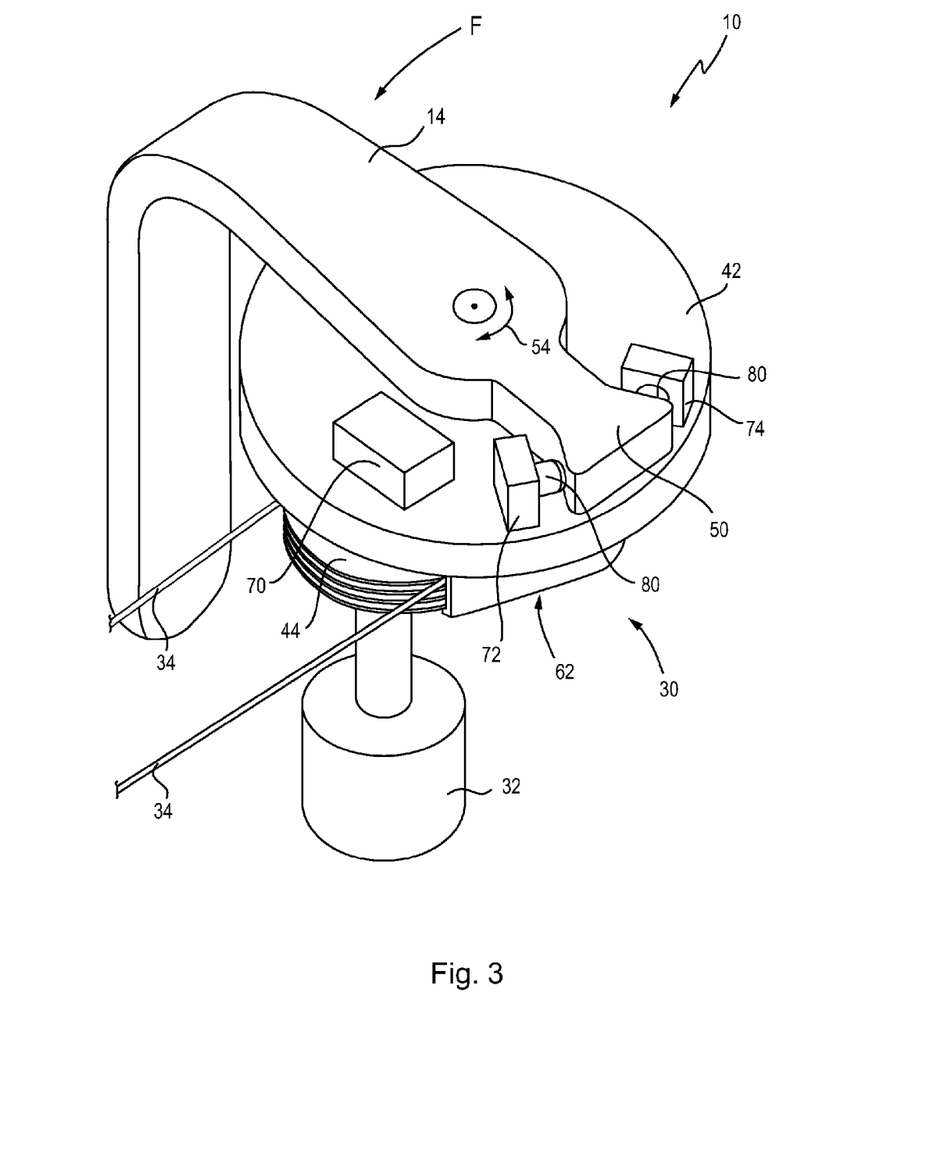
FIG. 3 shows the control element and adjustment element in a first embodiment.

FIG. 3 shows a first illustrative embodiment of a control element 14 and of an adjustment element 30. The parts of the adjustment element 30 that can be seen here are an at least approximately circular support element 42 and a cord pulley 44. The control element 14 is configured for the purpose of being able to be moved in a movement direction 54.

The control element 14 is operatively connected to the adjustment element 30, such that a force F applied to the control element 14 by the user can be transmitted to the adjustment element 30 via an abutment device 62 in order to move the adjustment element 30, in particular here to move the cord pulley 44.

The control element 14 has a portion 50. The portion 50 is here configured in one piece with the control element 14. An intermediate element 40 (not shown here) is hidden in this view by the control element 14.

The adjustment element 30 has the abutment device 62, which are arranged on the support element 42 in this embodiment. As can be seen in particular from FIGS. 4 and 5, the abutment device 62 defines a movement range 64 of the portion 50, and thus of the control element 14 as a whole, relative to the adjustment element 30.

The endoscopic instrument 10 also has a controller 70, which is configured to detect a measured value or a measured signal relating to a torsion of the first intermediate element 40 and to trigger the actuator 32, here an electric motor, on the basis of the measured value or the measured signal. To make the figure clearer, the electrical connection lines between the controller 70 and a measurement element 56 (not shown here) are not depicted. In another embodiment, the electrical connection is provided at least in part by a printed circuit board. The possible ways in which the actuator 32 is triggered, i.e. purely by motor, purely manually or by a combination of these, have already been explained in detail and will not be repeated here.

The abutment device 62 is here arranged in the circumferential direction of the support element 42. The abutment device 62 has a first abutment element 72 and a second abutment element 74, which are configured here as projections and between which an area of the portion 50 comes to lie. The abutment device 62 is adjustable in order to vary the one free rotatory movement range 64 of the portion 50, and thus the control element 14, relative to the adjustment element 30. For this purpose, the abutment elements 72, 74 here each have a symbolically indicated grub screw 80. The further the grub screws 80 are unscrewed from the respective abutment element 72, 74, the smaller the movement range 64 becomes.

Figure 4:
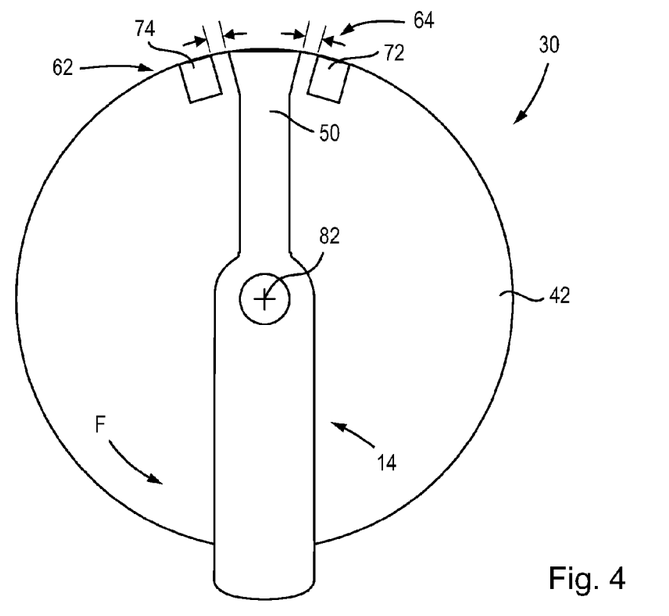
FIG. 4 shows the interaction of control element, adjustment element and abutment device in a second embodiment, in the free rotatory movement range of the control element relative to the adjustment element.

FIG. 4 shows a plan view of a second embodiment of control element 14 and adjustment element 30, corresponding in terms of its function to the first embodiment according to FIG. 3. If the control element 14 is moved relative to the adjustment element 30 only to such an extent that the free rotatory movement range 64 about a movement axis 82 is not exceeded, the portion 50 moves freely within the movement range 64. A force F applied to the control element 14 by the user does not transmit directly to the adjustment element 30. Instead, a torsion is detected in the intermediate element 40, and the actuator 32 is triggered to provide motorized movement of the adjustment element 30, here in particular of the cord pulley 44.

Figure 5:
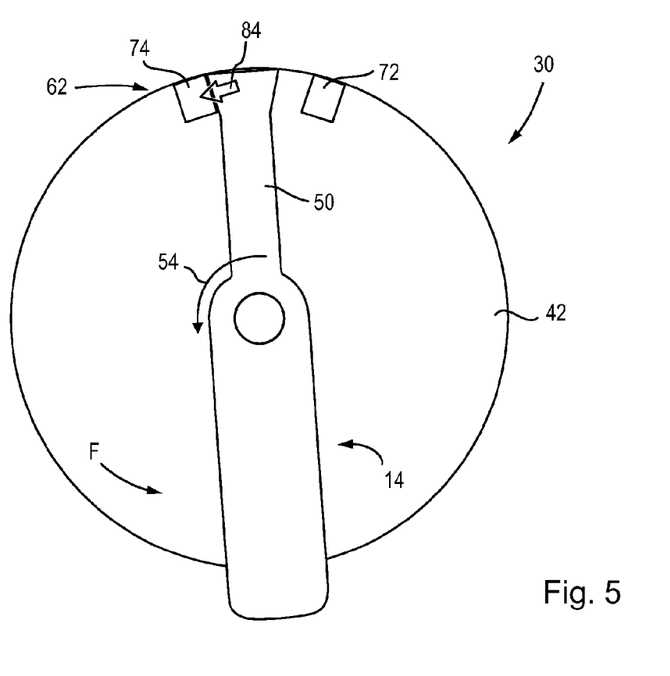
FIG. 5 shows the interaction of control element, adjustment element and abutment device in the second embodiment, when the free rotatory movement range is exhausted.

FIG. 5 shows the second embodiment according to FIG. 4 when the force applied by the user is so great that the combined operation sets in. It will be seen that the portion 50 has now exhausted the movement range 64, and at least some of the force F applied by the user via the control element 14 is transmitted from the portion 50 to the second abutment element 74 of the abutment device 62. This is symbolized by the arrow 84. If the user further increases the force F, this force is transmitted substantially via the portion 50 directly to the abutment device 62 and does not lead to any further torsion, or any appreciable further torsion, of the intermediate element 40. This provides overload protection for the intermediate element 40.

Figure 6:
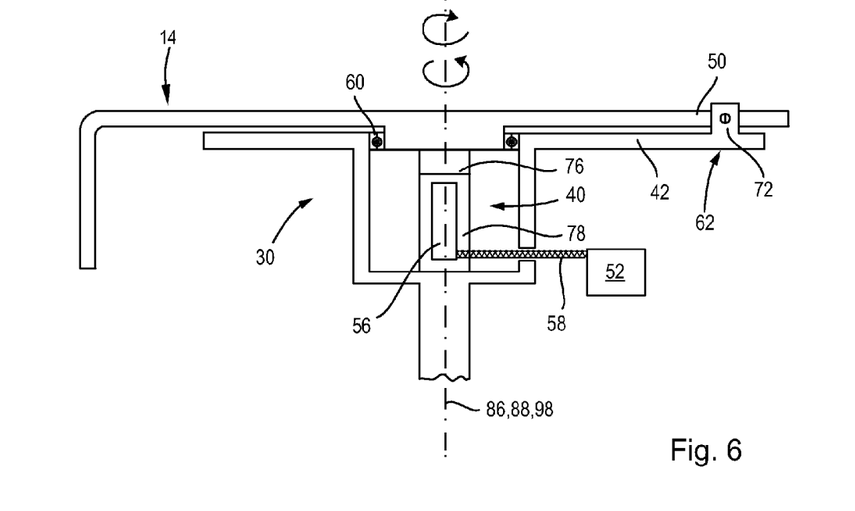
FIG. 6 shows an arrangement of the control element, adjustment element and intermediate element in a third embodiment.

FIG. 6 shows a partially cut-away view of control element 14, adjustment element 30 and intermediate element 40 in a third embodiment. A detection device 52 for detecting a torsion of the intermediate element 40 using a measurement element 56 is shown, wherein the measurement element 56 of the detection device 52 is arranged on the intermediate element 40. The measurement element 56 is configured in such a way that the electrical resistance of the measurement element 56 changes in the event of its shape changing. The measurement element 56 is configured here as a strain gauge. The measurement element 56 is connected to the detection device 52 by an electrical connection 58.

The intermediate element 40 here has a first area 76 and a second area 78, wherein the first area 76 is made from a different material than the second area 78. The second area 78 is here optimized with respect to the desired torsion measurement and made of PEEK. A first rotation axis 98 of the adjustment element 30, a second rotation axis 86 of the control element 14 and a longitudinal axis 88 of the intermediate element 40 coincide.

The control element 14 and the adjustment element 30 are coupled to each other via a bearing 60. The bearing is configured here as a ball bearing. This allows the control element 14 to be rotated easily about the first rotation axis 98 of the adjustment element 30.

Figure 7:
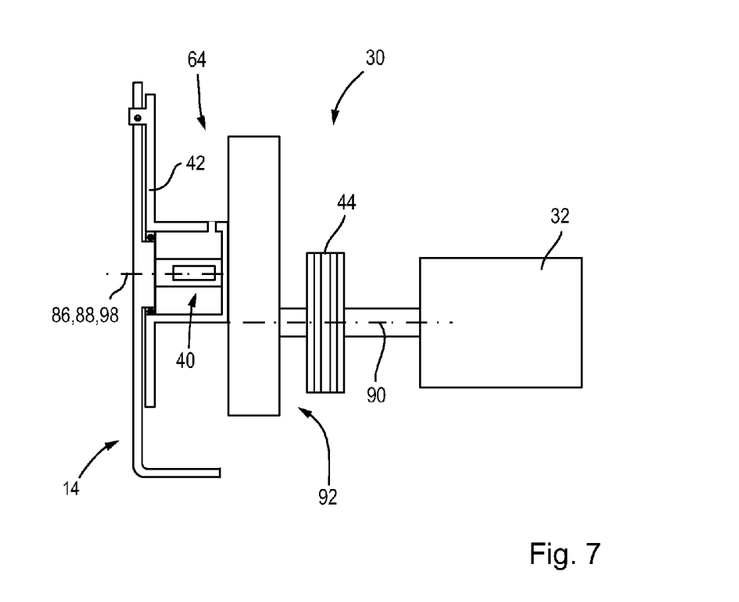
FIG. 7 shows an arrangement of control element, adjustment element, intermediate element and actuator in a fourth embodiment.

FIG. 7 shows a side view of control element 14, adjustment element 30, intermediate element 40 and actuator 32 in a fourth embodiment. A rotation axis 90 of the actuator 32 is indicated. The adjustment element 30 has a gear 92 here. As is illustrated in the following figure, this gear is a step-up gear 92, i.e. a rotation of the control element 14 about a first angle leads to a greater rotation of the cord pulley 44.

Figure 8:
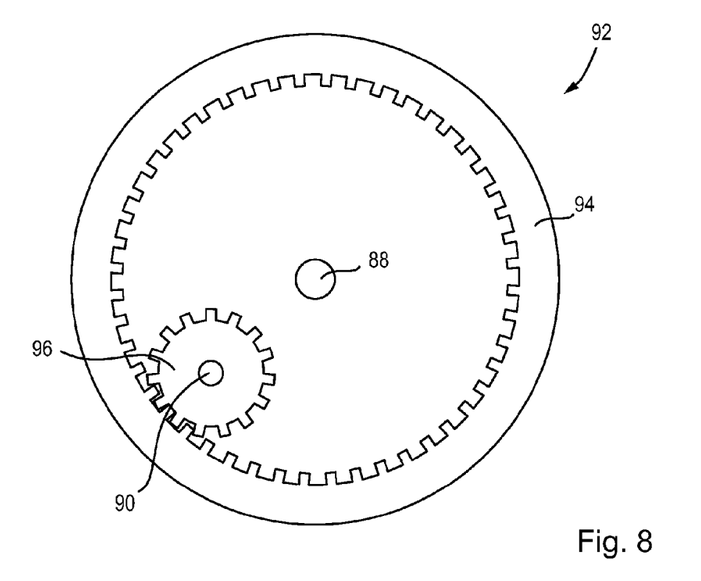
FIG. 8 shows a simplified view of the gear according to the third embodiment.

FIG. 8 shows an embodiment of the gear 92 according to FIG. 7. Here, the gear has an internal gear wheel 94 and a toothed wheel 96. By a suitable choice of the wheels 94, 96, a desired step-up can be easily obtained.

Figure 9:
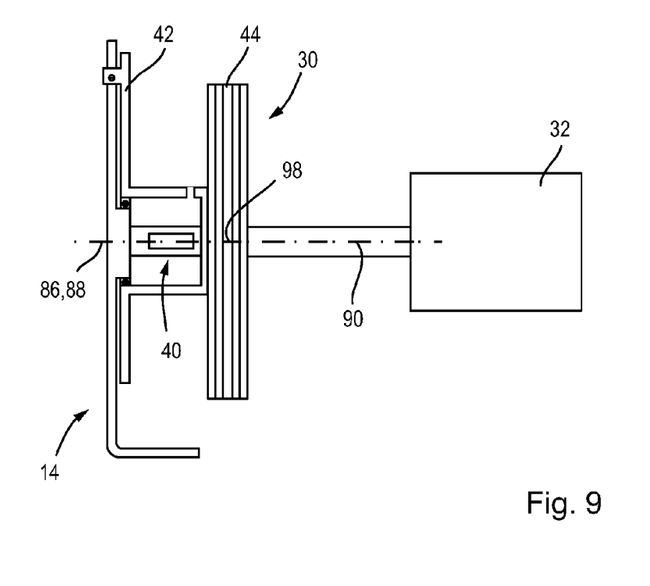
FIG. 9 shows an arrangement of control element, adjustment element, intermediate element and actuator in a fifth embodiment.

FIG. 9 shows a side view of control element 14, adjustment element 30, intermediate element 40 and actuator 32 in a fifth embodiment. In this embodiment, the rotation axis 90 of the actuator 32 and the first rotation axis 98 of the adjustment element 30 coincide. A further feature here is that the adjustment element 30 is configured as a cord pulley 44.

An endoscopic instrument 10 is disclosed that permits operation purely by motor, purely manually, or by a combination of the two. Moreover, in the event of a fault, it is ensured that the user can safely use the endoscopic instrument 10 without interruption and without restriction, despite lack of assistance from the actuator 32.

What is claimed is:
1. An endoscopic instrument, comprising:
a control section with a control element;
an instrument shaft with an actuatable portion, wherein the instrument shaft is connected to the control section;
an adjustment element;
a pull element, which is mechanically coupled to the adjustment element and to the actuatable portion of the instrument shaft, such that a movement of the adjustment element causes an actuation of the actuatable portion by a transmission of force via the pull element;
an actuator, which is coupled to the adjustment element, such that an actuation of the actuator causes the movement of the adjustment element by force transmission from the actuator to the adjustment element;
an intermediate element, which is operatively connected to the control element and to the adjustment element such that a force applied to the control element by a user is transmitted to the adjustment element via the intermediate element in order to move the adjustment element;
a detection device configured to detect a torsion of the intermediate element; and
an abutment device that includes a first abutment element and a second abutment element, the abutment device limiting free rotatory movement of the control element relative to the adjustment element to a movement range defined between the first abutment element and the second abutment element;
wherein the intermediate element extends along a rotation axis and is rotatable about the rotation axis.
2. The endoscopic instrument of claim 1, wherein the detection device includes a measurement element arranged on the intermediate element.
3. The endoscopic instrument of claim 1, wherein the detection device includes a measurement element which is configured in such a way that an electrical resistance of the measurement element changes when a shape of the measurement element changes.
4. The endoscopic instrument of claim 1, wherein the detection device includes a measurement element configured as a strain gauge.
5. The endoscopic instrument of claim 1, wherein the detection device includes at least two measurement elements which are arranged in such a way that, in the detection device, a compensation is permitted for at least one interference chosen from the group consisting of flexion, longitudinal extension and temperature.
6. The endoscopic instrument of claim 1, wherein the intermediate element includes at least a first area and a second area, wherein the first area is made from a different material than the second area.
7. The endoscopic instrument of claim 1, wherein the intermediate element is made from a different material than the control element.

8. The endoscopic instrument of claim 1, wherein the intermediate element is made from a different material than the adjustment element.

9. The endoscopic instrument of claim 1, wherein the abutment device is adjustable, in order to vary the movement range.

10. The endoscopic instrument of claim 1, wherein the adjustment element includes a gear.

11. The endoscopic instrument of claim 1, wherein the adjustment element includes a gear with a positive transmission ratio.

12. The endoscopic instrument of claim 1, wherein a first rotation axis of the adjustment element, a second rotation axis of the control element, and a longitudinal axis of the intermediate element coincide.

13. The endoscopic instrument of claim 1, wherein a first rotation axis of the adjustment element and a third rotation axis of the actuator coincide.

14. The endoscopic instrument of claim 1, wherein the adjustment element has an at least approximately circular support element, on which the abutment device is arranged at least approximately in a circumferential direction of the at least approximately circular support element.

15. The endoscopic instrument of claim 1, further comprising a controller configured to detect a measured value of the torsion of the intermediate element and to trigger the actuator based on the measured value.

16. The endoscopic instrument of claim 1, wherein the adjustment element includes an at least approximately circular support element extending circumferentially about the rotation axis; and wherein the first abutment element and the second abutment element are disposed at different circumferential positions on the support element such that a circumferential distance is defined therebetween.

17. The endoscope instrument of claim 16, wherein the movement range corresponds to the circumferential distance defined between the first abutment element and the second abutment element.

18. The endoscope instrument of claim 16, wherein the first abutment element and the second abutment element each extend from the support element in a direction parallel to the rotation axis;

wherein the control element includes an end portion that extends in a direction at least substantially perpendicular to the rotation axis; and wherein the end portion of the control element is positioned between the first abutment element and the second abutment element, and is pivotable about the rotation axis between a first position, in which the end portion contacts the first abutment element, and a second position, in which the end portion contacts the second abutment element.

* * * * *